(12) United States Patent
Govari

(10) Patent No.: US 11,571,260 B2
(45) Date of Patent: Feb. 7, 2023

(54) PRE-OPERATIVE REGISTRATION OF ANATOMICAL IMAGES WITH A POSITION-TRACKING SYSTEM USING ULTRASOUND MEASUREMENT OF SKIN TISSUE

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 139 days.

(21) Appl. No.: 16/836,633

(22) Filed: Mar. 31, 2020

(65) Prior Publication Data
US 2021/0298832 A1    Sep. 30, 2021

(51) Int. Cl.
*A61B 5/05*    (2021.01)
*A61B 34/20*    (2016.01)
*G06T 7/70*    (2017.01)

(52) U.S. Cl.
CPC .............. *A61B 34/20* (2016.02); *G06T 7/70* (2017.01); *A61B 2034/2051* (2016.02);
(Continued)

(58) Field of Classification Search
None
See application file for complete search history.

(56) References Cited

U.S. PATENT DOCUMENTS

| 5,391,199 A | 2/1995 | Ben-Haim |
| 6,106,464 A | 8/2000 | Bass et al. |

(Continued)

FOREIGN PATENT DOCUMENTS

| EP | 3454299 | 3/2019 |
| WO | WO9605768 | 2/1996 |

OTHER PUBLICATIONS

International Search Report dated Jul. 8, 2021 from corresponding PCT Patent Application No. PCT/IB2021/052565.
(Continued)

*Primary Examiner* — Joel F Brutus
(74) *Attorney, Agent, or Firm* — Frost Brown Todd LLP

(57) ABSTRACT

A method includes, receiving multiple measurements, which are acquired using a registration tool including an ultrasound (US) transducer and a position sensor of a position-tracking system. The measurements are acquired by positioning the registration tool, while maintaining a gap from skin tissue, at multiple respective locations on a patient head and acquiring respective position measurements of the position sensor and respective US measurements of the skin tissue at the locations. First positions, of the skin tissue at the multiple locations, are calculated based on the position measurement and the US measurements obtained using the registration tool. Second positions, of the skin tissue at the multiple locations, are identified in an anatomical image of the patient head. The anatomical image is registered with a coordinate system of the position tracking system, by correlating the first positions and the second positions, so as to enable tracking a medical instrument, which is inserted into the patient head and includes another position sensor of the position-tracking system, using the anatomical image registered with the position-tracking system.

20 Claims, 2 Drawing Sheets

(52) U.S. Cl.
CPC ............ *A61B 2034/2063* (2016.02); *A61B 2034/2065* (2016.02); *A61B 2034/2072* (2016.02); *A61B 2560/0223* (2013.01); *A61B 2560/0242* (2013.01); *G06T 2207/10072* (2013.01); *G06T 2207/30201* (2013.01)

(56) References Cited

U.S. PATENT DOCUMENTS

| | | |
|---|---|---|
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2014/0187955 A1 | 7/2014 | Kang |
| 2014/0276020 A1 | 9/2014 | Hutchins et al. |
| 2018/0098816 A1* | 4/2018 | Govari ................ A61B 8/085 |
| 2019/0046154 A1 | 2/2019 | Govari et al. |
| 2019/0108645 A1* | 4/2019 | Ben-Yishai ............ A61B 34/10 |
| 2019/0192228 A1 | 6/2019 | Salazar et al. |

OTHER PUBLICATIONS

Maurer, Calvin R et al., "AcouStick: A Tracked A-Mode Ultrasonography System for Registration in Image-Guided Surgery", Jan. 1, 2006, Medical Image Computing and Computer Assisted Intervention—Miccai '99: Second International Conf., Cambridge UK, Sep. 16-22, 1999; Lecture Notes in Computer Science: 1679, Springer, Berlin (U.A.) pp. 953-962.

* cited by examiner

PRE-OPERATIVE REGISTRATION OF ANATOMICAL IMAGES WITH A POSITION-TRACKING SYSTEM USING ULTRASOUND MEASUREMENT OF SKIN TISSUE

FIELD OF THE INVENTION

The present invention relates generally to image guided medical procedures, and particularly to methods and systems for registration of an anatomical image with a position-tracking system.

BACKGROUND OF THE INVENTION

Ultrasound (US) transducers and position-tracking systems may be used in various medical applications, such as in image guided procedures.

For example, U.S. Patent Application Publication 2019/0192228, issued as U.S. Pat. No. 10,786,311 on Sep. 29, 2020, describes an array of sensors that may be used to perform touchless registration of landmarks of a patient's face before an ENT procedure in order to associate those landmarks with pre-operative images in three-dimensional space, which is required for image guided surgery features such as navigation. Touchless or light-touch registration may improve accuracy by avoiding the need for substantial pressing against a patient's skin, which may deform and thereby introduce erroneous registration data. A sensor may also be implemented in forms other than an array such as handheld probe having a single sensor as opposed to an array.

U.S. Patent Application Publication 2019/0192228, issued as U.S. Pat. No. 10,786,311 on Sep. 29, 2020, describes a method and apparatus for performing facial registration includes hovering a registration probe over a plurality of target locations on a face of a patient. An ultrasonic wave is emitted from the registration probe at each of the target locations and a return of the ultrasonic wave is received from each of the target locations. A magnetic signal is received by the registration probe from a magnetic emitter located proximate to the face of the patient to identify a location in space of the registration probe relative to the magnetic emitter. The target location of the received ultrasonic return is correlated to a location identified in space relative to the magnetic emitter.

SUMMARY OF THE INVENTION

An embodiment of the present invention that is described herein provides a method, including receiving multiple measurements, which are acquired using a registration tool including an ultrasound (US) transducer and a position sensor of a position-tracking system. The measurements are acquired by positioning the registration tool, while maintaining a gap from skin tissue, at multiple respective locations on a patient head and acquiring respective position measurements of the position sensor and respective US measurements of the skin tissue at the locations. First positions, of the skin tissue at the multiple locations, are calculated based on the position measurement and the US measurements obtained using the registration tool. Second positions, of the skin tissue at the multiple locations, are identified in an anatomical image of the patient head. The anatomical image is registered with a coordinate system of the position tracking system, by correlating the first positions and the second positions, so as to enable tracking a medical instrument, which is inserted into the patient head and includes another position sensor of the position-tracking system, using the anatomical image registered with the position-tracking system.

In some embodiments, the method includes acquiring respective position measurements of the position sensor and respective US measurements of bone tissue at the locations, calculating the first positions includes calculating first bone positions of the bone tissue at the multiple locations, and identifying the second positions includes identifying second bone positions of the bone tissue at the multiple locations. In other embodiments, the US transducer is disposed at a fixed displacement relative to the position sensor, and calculating the first positions includes considering the fixed displacement in calculation of the first positions. In yet other embodiments, the anatomical image includes one or more computerized tomography (CT) images.

In an embodiment, the locations include locations of skin tissue covering bone features selected from a list consisting of a cheek bone protrusion, a bridge of a nose, a tip of the nose and a chin. In another embodiment, the position-tracking system includes a magnetic position-tracking system. In yet another embodiment, receiving the US measurements includes receiving round-trip propagation times of US pulses traversing, at one or more of the locations, between a tip of the registration tool and the skin tissue of the patient head.

In some embodiments, the locations include locations of skin tissue covering bone features, so that receiving the US measurements includes receiving given round-trip propagation times of US pulses traversing, at one or more of the locations, between a tip of the registration tool and the bone features of the locations, and the method includes, using the given round-trip propagation times for registering the anatomical image with the coordinate system of the position tracking system. In other embodiments, the medical instrument includes a sinuplasty catheter.

In an embodiment, the registration tool includes a handheld wand. In another embodiment, the multiple measurements are acquired at a given temperature and a given humidity, and the method includes calibrating the registration tool to compensate for a change in the US measurements caused by a deviation from at least one of the given temperature and the given humidity.

There is additionally provided, in accordance with an embodiment of the present invention, an apparatus including a registration tool and a processor. The registration tool includes an ultrasound (US) transducer and a position sensor of a position-tracking system. The US transducer is configured, when the registration tool is positioned sequentially, while maintaining a gap from skin tissue, at multiple respective locations on a patient head, to acquire respective US measurements of the skin tissue at the locations. The position sensor is configured to acquire respective position measurements of the registration tool at the locations. The processor is configured to: (a) receive the multiple US measurements and the respective position measurements acquired by the registration tool, (b) calculate first positions of the skin tissue at the multiple locations, based on the position measurements and the US measurements, (c) identify second positions of the skin tissue at the multiple locations, in an anatomical image of the patient head, and (d) register the anatomical image with a coordinate system of the position tracking system, by correlating the first positions and the second positions, so as to enable tracking a medical instrument, which is inserted into the patient head and includes another position sensor of the position-tracking system, using the anatomical image registered with the position-tracking system.

The present invention will be more fully understood from the following detailed description of the embodiments thereof, taken together with the drawings in which:

DETAILED DESCRIPTION OF EMBODIMENTS

Overview

Figure 1:
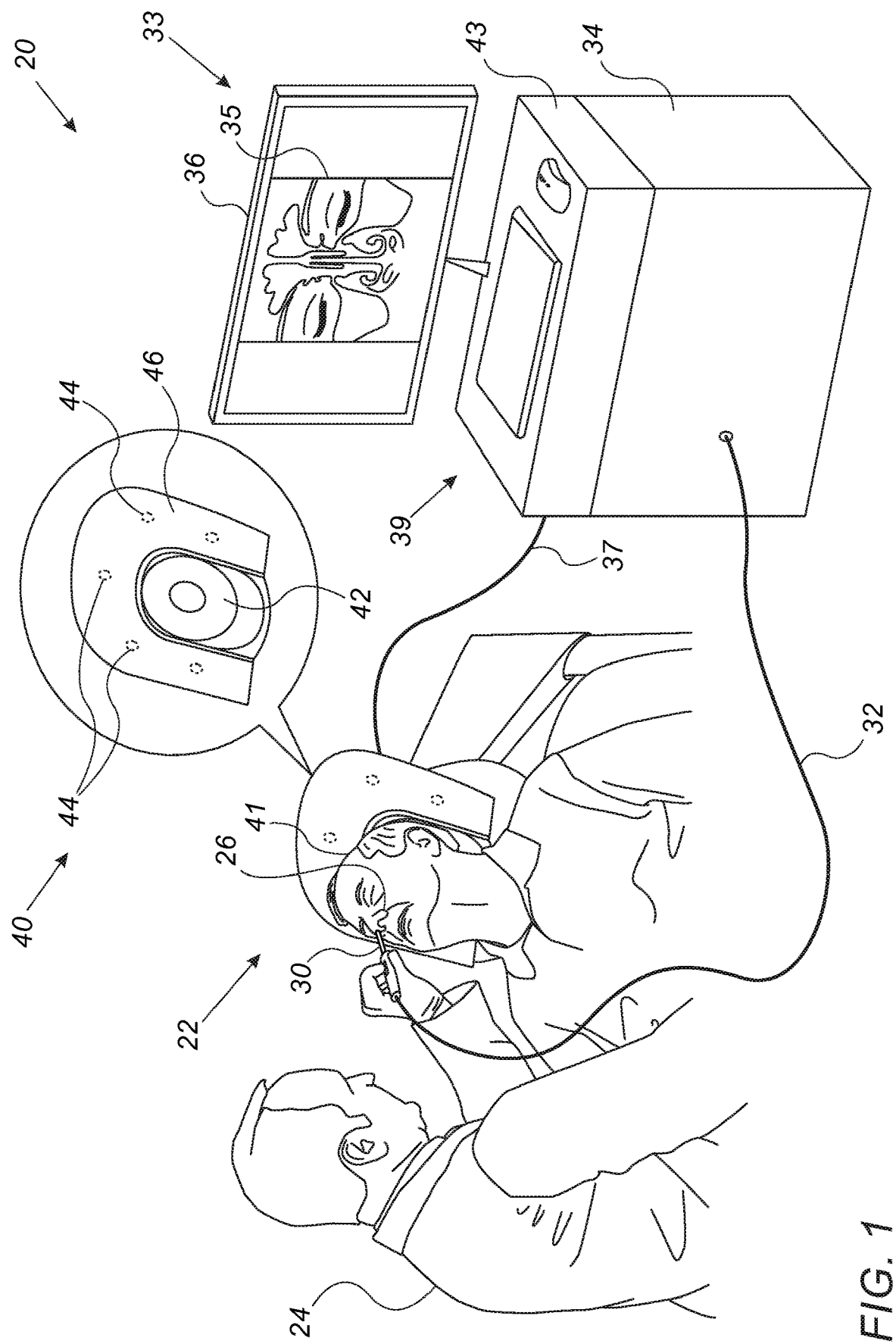
FIG. 1 is a schematic, pictorial illustration of a sinuplasty surgical system, in accordance with an embodiment of the present invention.

Some medical procedures, such as sinuplasty, require registration of an anatomical image of organs in question with a coordinate system of a position tracking system. Using the registration, a surgical tool fitted with a position sensor is navigated to the treated organs, and is visualized overlaid on the anatomical image.

In principle, the registration may be carried out using some external registration tool fitted with a position sensor of the position tracking system. Such a tool could be brought into physical contact with preselected locations on the patient face (e.g., nose tip, bridge of the nose, and centers of the two cheeks). The anatomical image could then be registered to the coordinate system of the position tracking system based on the measured positions of bone tissue at the preselected locations.

This possible solution, however, is likely to be inaccurate and unsuitable for sinuplasty procedures, in which it is typically important to obtain registration of the anatomical image at accuracy level better than 1 mm. Due to the uncontrolled pressure applied, by the registration tool, to soft tissue in the patient face, the accuracy of this hypothetical solution may become insufficient.

Embodiments of the present invention that are described hereinbelow provide improved techniques for registering an anatomical image (e.g., a two-dimensional slice of a three-dimensional computerized tomography image) with the coordinate system of a position-tracking system. In some embodiments, a registration tool comprises an ultrasound (US) transducer and a position sensor of the position-tracking system that are fitted, within the registration tool, at a predefined distance from one another. In order to perform registration, an operator (e.g., a physician) positions the registration tool, while maintaining a gap (typically an air gap of several millimeters) from skin tissue of the patient, at multiple predefined locations on the patient's head. At each of the predefined locations, the following measurements are performed:

The position tracking system measures the position and orientation of the position sensor fitted in the registration tool.

The registration tool measures a distance between the US transducer and the skin tissue at the respective location.

In some embodiments, a processor uses these measurements to calculate, for each of the predefined locations on the patient's head, the position of the respective skin tissue in the coordinate system of the position tracking system.

For a given predefined location on the patient's head, the output of the US transducer is indicative of the gap between the US transducer and the skin tissue. The relative displacement (if any) between the US transducer and the position sensor is fixed and known, and the position of the position sensor has been measured in the coordinate system of the position tracking system. Therefore, the processor uses the aforementioned measurements to calculate the position of the skin tissue in the coordinate system of the position tracking system. This position is referred to herein as the "US coordinate" of the skin tissue, or as the "US skin coordinate," for the predefined location on the patient head. The above procedure is repeated for some or all of the multiple predefined locations, to produce a set of US coordinates.

In addition, the processor identifies the positions of the skin tissue at the predefined multiple locations in a pre-acquired computerized tomography (CT) image. These identified positions are referred to herein as "CT coordinates" of the skin tissue, or as "CT skin coordinates." The processor then registers the CT image with the coordinate system of the position tracking system, e.g., by calculating a geometrical transformation that matches the US skin coordinates with the respective CT skin coordinates.

Note that the disclosed registration process is based on measurements of the skin tissue while maintaining the gap between the registration tool and the skin tissue. In other words, during the measurements the registration tool does not touch the skin tissue. Therefore, the registration is accurate because the registration tool does not make any distortion in the skin tissue in question.

The disclosed techniques enable improved navigation of a sinuplasty surgical tool, which is inserted into the patient head and comprises another position sensor of the position-tracking system.

System Description

FIG. 1 is a schematic pictorial illustration of a sinuplasty surgical system 20, in accordance with an embodiment of the present invention. System 20 comprises a magnetic position tracking system, which is configured to track the position of one or more position sensors in the head of a patient 22. The magnetic position tracking system comprises magnetic field-generators and one or more position sensors (all described in detail below). The position sensors generate position signals in response to sensed external magnetic fields from the field generators, thereby enabling a processor 34 to map the position of each sensor in the coordinate system of the position tracking system as will be described below.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004; 2003/0120150 A1, issued as U.S. Pat. No. 7,729,742 on Jun. 1, 2010; and 2004/0068178 A1, now abandoned, whose disclosures are all incorporated herein by reference.

In the present example, system 20 comprises a location pad 40, which comprises multiple field-generators 44 fixed on a frame 46. In the exemplary configuration shown in FIG. 1, pad 40 comprises five field-generators 44, but in other embodiments, pad 40 may comprise any other suitable number of generators 44. Pad 40 further comprises a pillow 42 placed under a head 41 of patient 22, such that generators 44 are located at fixed, known positions external to the patient. System 20 further comprises a console 33, which comprises processor 34 and a driver circuit (not shown) configured to drive field-generators 44 with suitable signals so as to generate magnetic fields in a predefined working volume around head 41.

In an embodiment, processor 34 is typically a general-purpose processor of a general-purpose computer. Processor 34 comprises suitable front end and interface circuits for receiving data from external sources, as well as measurements from wand 30, via a cable 32, and for controlling other components of system 20.

In some embodiments, console 33 comprises a driver circuit 43 configured to drive, via a cable 37, field-generators 44 with suitable signals so as to generate magnetic fields in a predefined working volume in space around head 41. Console 33 further comprises input devices 39 and a user display 36, which is configured to display the data to any user of system 20.

In some embodiments, system 20 comprises a registration tool, such as a handheld wand 30, which is used by system 20 for registering the coordinate system of the magnetic position tracking system with that of a pre-acquired a computerized tomography (CT) image described below. The registration tool is configured to acquire ultrasound and position measurements, and is depicted in detail in FIG. 2 below.

Typically, a physician 24 positions wand 30 sequentially at multiple predefined locations on an external surface (e.g., skin tissue) of patient head 41, while maintaining a gap from skin tissue. Each predefined location is typically chosen to be an easily identifiable feature on head 41, such as a cheek bone protrusion, a bridge of a nose 26 (located between the eyes of patient 22), a tip of nose 26, a chin, or any other suitable identifiable feature.

In an embodiment, processor 34 receives a CT image 35 obtained using an external CT system (not shown). Processor 34 uses image 35 to form a surface image of at least part of patient head 41. In some embodiments, processor 34 is configured to use hounsfield units (HU) for determining the radiodensity of skin and possibly of bones. For example, HU ranging between −200 and 500 may be used by processor 34 for muscular tissue and skin, and HU ranging between 700 and 3000 may be used for determining the radiodensity of bones in the patient face.

In some embodiments, processor 34 is configured to compare these HU figures with HU of −1000, which is a standard scale for air, so as to determine boundaries of the patient face. In an alternative embodiment, HU above 500 may be used for determining the radiodensity of bones, HU of −200 and below may be used for air, and HU ranging between −200 and 500 may be used for muscular tissue and skin.

In alternative embodiments, any other suitable values can be used. Further alternatively, processor 34 may distinguish between different types of tissue in the CT image, and in particular identify skin tissue and possibly bone tissue, using any other suitable criterion or technique.

In an embodiment, when placed at a predefined location on the patient head, while maintaining a gap from skin tissue at the redefined location, wand 30 is configured to (i) acquire US measurements of skin tissue, and (ii) generate position signals indicative of the position of this predefined location in the coordinate system of the magnetic position tracking system. The acquisition of the skin tissue measurements by wand 30 is described in detail in FIG. 2 below.

In some embodiments, processor 34 is configured to calculate two coordinates for each predefined location on the patient head—A "US coordinate" and a "CT coordinate." The US coordinate is derived from the US and position measurements of wand 30 at this predefined location, and is indicative of the coordinate of the skin tissue at this location in the coordinate system of the magnetic position tracking system. The CT measurement is indicative of the coordinate of the skin tissue at this location, as identified in the CT image.

In an embodiment, processor 34 is configured to correlate between the US coordinates and the CT coordinates of the skin at the predefined locations in image 35, so as to register the CT image with the coordinate system of the position tracking system.

In some embodiments, in addition to acquiring US measurements of skin tissue, processor 34 is configured to apply the technique described above, mutatis mutandis, for acquiring US measurements of bone tissue, also referred to herein as given round-trip propagation times. In such embodiments, processor 34 is configured to correlate between the US coordinates and the CT coordinates of the bone at the predefined locations in image 35, so as to register the CT image with the coordinate system of the position tracking system.

The registration process is typically performed before the actual sinuplasty procedure. During the sinuplasty procedure, physician 24 may insert into head 41 a medical device (not shown), such as a sinuplasty balloon catheter or any other suitable ear nose throat (ENT) tool, which comprises an additional position sensor of the position-tracking system. Since the CT image is already registered with the position-tracking system, physician 24 may navigate the medical device whose distal end is displayed on the CT image, to a target location in head 41.

In alternative embodiments, instead of CT image 35, processor 34 is configured to receive one or more images acquired using another suitable anatomical imaging technique, such as but not limited to fluoroscopy or magnetic resonance imaging (MRI), and to register these anatomical images with the coordinate system as described above.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

This particular configuration of system 20 is shown by way of example, in order to illustrate certain problems that are addressed by embodiments of the present invention, and to demonstrate the application of these embodiments in enhancing the performance of such a system. Embodiments of the present invention, however, are by no means limited to this specific sort of example system, and the principles described herein may similarly be applied to other sorts of medical and/or registration systems. For example, embodiments described in FIG. 1 above, and embodiments described in FIGS. 2 and 3 below, may be applied for registering between two or more coordinate systems of any soft tissue, in addition to or instead of the facial skin of patient 22.

Registering Anatomical Images With a
Position-Tracking System Using Ultrasound

Figure 2:
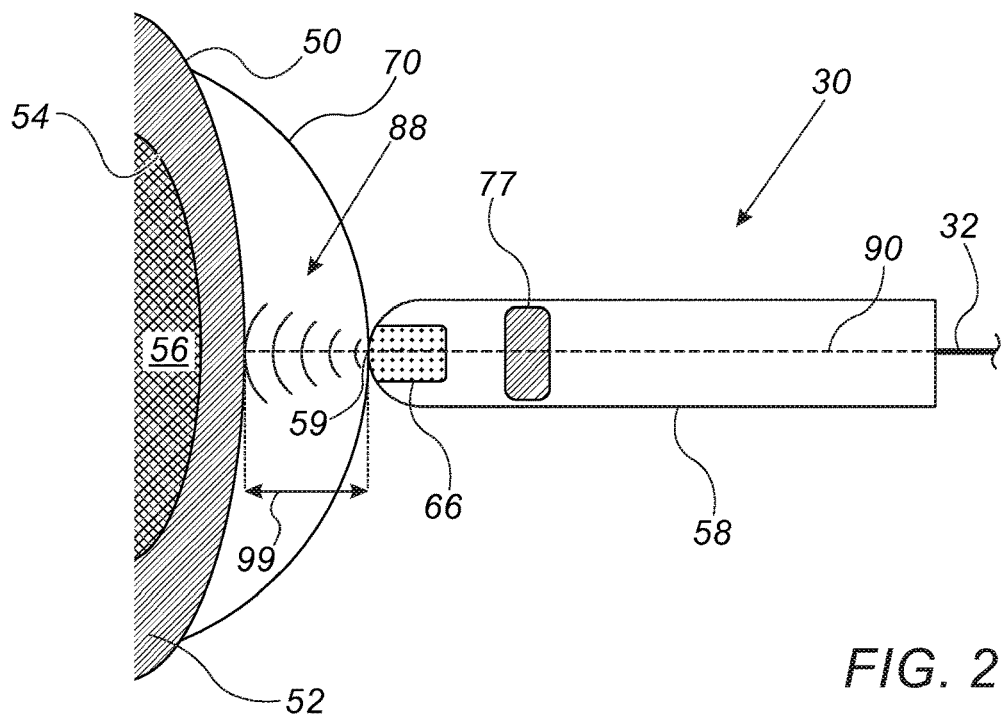
FIG. 2 is a schematic, pictorial illustration of a registration tool, in accordance with an embodiment of the present invention.

FIG. 2 is a schematic, pictorial illustration of wand 30, in accordance with an embodiment of the present invention. In some embodiments, physician 24 positions wand 30 at one of the multiple predefined locations on patient head 41, while maintaining a gap 99 (e.g., between a few millimeters and about 1-2 cm) between a tip 59 of wand 30 and skin tissue 50. Note that gap 99 between tip 59 and skin tissue 50 may have any suitable type of fluid, such as but not limited to (a) air or any other type of gas, (b) gel or any other type of liquid, or (c) any suitable combination of gas and liquid.

For the sake of conceptual clarity, the description below assumes having solely air within gap 99, however, all the embodiments and techniques described below are applicable, mutatis mutandis, to any suitable type of one or more fluids positioned within gap 99.

In the context of the present disclosure and in the claims, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 100%.

In some embodiments, wand 30 comprises a housing 58, which contains a position sensor 77 and an ultrasound (US) transducer 66. In the example of FIG. 2, position sensor 77 and US transducer 66 are positioned at different locations within wand 30. In other embodiments, position sensor 77 and
US transducer 66 may be arranged within wand 30 using any other suitable configuration, such as but not limited to having position sensor 77 disposed concentrically around and US transducer 66.

In some embodiments, US transducer 66 is configured to produce US pulses 88 into the tissue. FIG. 2 shows example tissue structure, which comprises skin tissue 50, intermediate tissue 52, bone tissue 56 and an interface layer 54 between tissue 52 and 56.

In an embodiment, a registration between the coordinate systems of the CT and the position tracking system is typically carried out before performing the sinuplasty procedure. In such embodiments, in the pre-operative registration, physician 24 positions wand 30 at gap 99 from one or more of the multiple predefined locations on patient head 41, for example, from the tip of nose 26.

In an embodiment, physician 24 commands processor 34 (e.g., using input devices 39) to activate transducer 66 so as to produce US pulses 88 that are transmitted along an axis 90 of wand 30. When wand is positioned at gap 99 from skin tissue 50, US pulses 88 traverse through the air of gap 99. Subsequently a first portion (e.g., at least part) of US pulses 88 are reflected from skin tissue 50 and travel through the air of gap 99, back to wand 30.

In some embodiments, a second portion of US pulses 88, which is not reflected from skin tissue 50, travels through skin tissue 50 and intermediate tissue 52 toward interface layer 54 and bone tissue 56. In such embodiments, US pulses 88 are reflected from interface 54 and travel through tissue 52 and skin tissue 50, back to wand 30.

In some embodiments, wand 30 is configured to sense the first reflected portion of US pulses 88 (reflected from skin tissue 50) and the second reflected portion of US pulses 88 (reflected from interface 54), and to send (e.g., via cable 32) to processor 34, a signal indicative of at least the time and amplitude of the first and second reflected portions of US pulses 88.

In some embodiments, processor 34 is configured to measure round-trip propagation times of each of the first and second portions of the US pulses, also denoted first and second time-of-flight (TOF), respectively. Based on the known speed of US pulses 88 in air, in tissue 52 and in skin tissue 50, processor 34 is configured to translate the measured first and second TOFs into (a) a size of gap 99, and (b) a distance between tip 59 and bone tissue 56. In such embodiments, wand is configured to transmit the position measurements obtained from position sensor 77, and the TOF measured using US transducer 66, via cable 32, to processor 34.

The speed of US pulses 88 in air may slightly change with the temperature and/or with humidity of the air within gap 99. In some embodiments, system 20 may comprise a jig 70 for calibrating wand 30 before performing the registration procedure. Jig 70 is configured to position tip 59 at a known gap from a suitable US receiver (not shown), and to have air at different temperatures and humidity levels, so as to calibrate wand 30. In the example of FIG. 2, jig 70 has a dome-shape configured to make physical contact with head 41 at multiple positions sufficiently-far (e.g., at a distance larger than 5 cm) from wand 30, and therefore, jig 70 does not affect the measurements acquired by wand 30. Moreover, jig 70 comprises materials transparent to US pulses 88, so that jig 70 has a negligible impact on the measurements acquired by wand 30. In such embodiments, processor 34 is configured to calibrate the measurements of wand 30 before performing the registration procedure.

The configuration of jig 70 is simplified and schematic, and is provided by way of example for the sake of conceptual clarity. In other embodiments, jig 70 may have any other suitable shape and method for positioning tip 59 at a known gap from skin tissue 50. During the registration procedure, processor 34 may receive signals indicative of the temperature and humidity of the air in close proximity to the tissue in question, and, based on the calibration, to compensate for any deviation from at least one of the temperature and humidity.

In some embodiments, system 20 may comprise multiple jigs or an adjustable jig, which are configured to position tip 59 at respective known gaps from a suitable US receiver, or from any other suitable apparatus for detecting and/or reflecting US pulses. In such embodiments, processor 34, or any other controller of wand 30, is configured to calibrate wand 30 for a range of gaps 99, so that the registration process is sufficiently accurate when physician 24 positions wand 30 at different gaps 99.

Because head 41, and particularly facial organs, may comprise, in the predefined locations, soft tissue that deforms naturally (e.g., due to changes in liquid level in the cheeks along the day), it is important to have measurements that are independent of the natural deformation of these soft tissues.

In the embodiments described above, wand 30 is configured to produce signals for measuring the distance between tip 59 of US transducer 66 and bone tissue 56 at the predefined locations. In some embodiments, processor 34 is configured, based on the measured distance to bone tissue 56, to calculate for each of the predefined locations on patient's head 41, the position of the respective bone tissue in the coordinate system of the position tracking system. This position is also referred to herein as the "US bone coordinate." Similarly, processor 34 is configured to identify the positions of bone tissue 56 at the predefined multiple locations in the pre-acquired CT image, also referred to herein as "CT bone coordinates." In some embodiments, based on the "US bone coordinate" and respective "CT bone coordinate," processor 34 is configured to register the CT image with the coordinate system of the position tracking system. Thus, the registration process is not affected by the any natural deformation of soft tissue in patient's head 41. Moreover, the disclosed techniques are not sensitive to any deformation of soft tissue, natural (e.g., due to the aforementioned changes in liquid level) or artificial (e.g., due to pressure applied by the registration tool).

Additional registration methods between anatomical images and position tracking systems, which are based on bone coordinates, are described in detail, for example, in U.S. Patent Application Publication 2018/0098816, now abandoned, whose disclosure is incorporated herein by reference.

In the configuration of wand 30 shown in FIG. 2, position sensor 77 is fitted at a fixed, known displacement relative to transducer 66, thus, processor 34 is configured to take into account the fixed displacement in calculating the US skin coordinates and the US bone coordinates.

In the operational mode shown in FIG. 2, tip 59 is positioned at gap 99 from skin tissue 50, and therefore does not apply pressure to, and does not deform skin tissue 50 or any other tissue of patient 22. In some embodiments, based on this operational mode, processor 34 is configured to carry out the registration process between the US skin coordinates and the CT skin coordinates, without any distortion caused by the soft tissue.

In some embodiments, processor 34 is configured to perform the registration based on: (a) the skin coordinates, (b) the bone coordinates, or a suitable combination thereof. For example, in case the position of skin tissue in the CT image is not sufficiently clear in a given location of the predefined locations, processor 34 may use the US bone coordinate and the CT bone coordinate for the registration at the given location. In this example, processor 34 is configured to (a) perform the registration based on the bone coordinates of all the predefined locations, or (b) perform the registration based on the bone coordinates only in the given point, and use the skin coordinates for calculating the registration in all predefined locations other than the given location.

Figure 3:
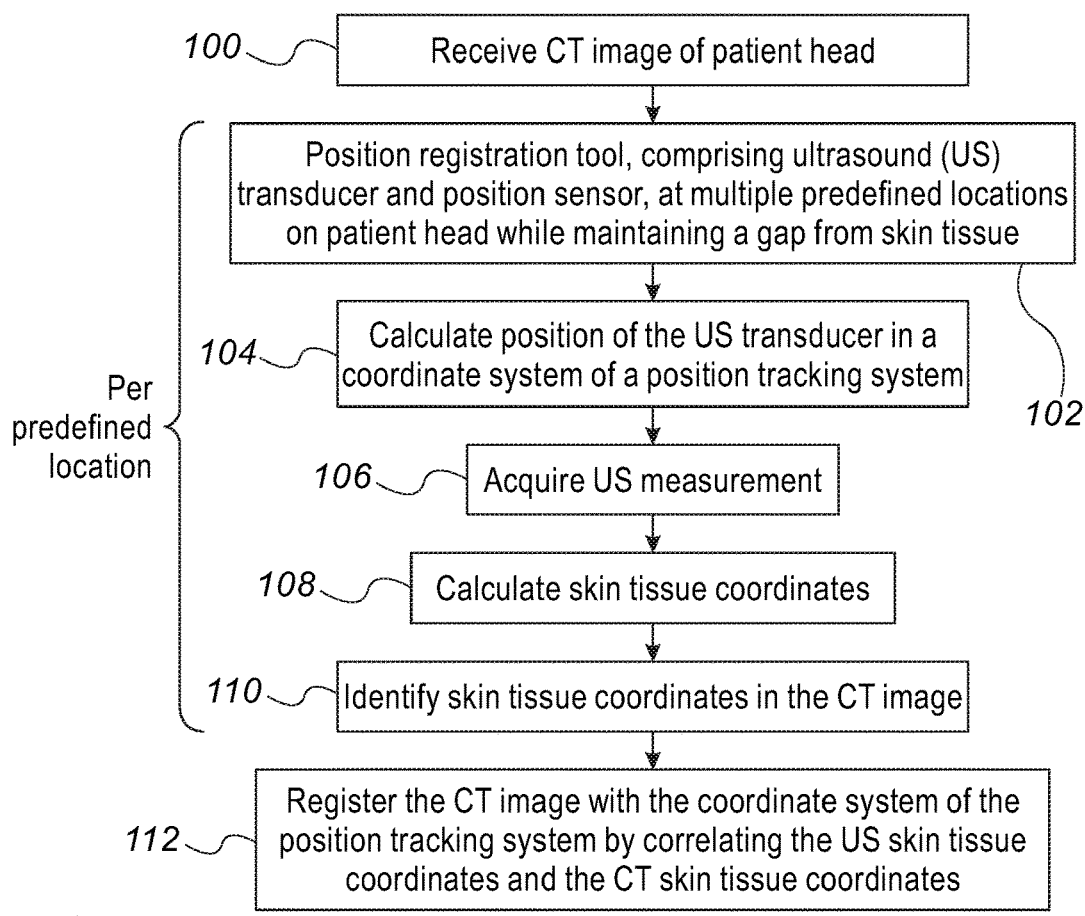
FIG. 3 is a flow chart that schematically illustrates a method for registering an anatomical image with a coordinate system of a position tracking system, in accordance with another embodiment of the present invention.

FIG. 3 is a flow chart that schematically illustrates a method for registering CT image 35 with the coordinate system of the position tracking system, in accordance with another embodiment of the present invention. The method begins with a CT image acquisition step 100, in which processor 34 receives one or more CT images that capture at least skin tissue (referred to herein as CT skin images) and may also capture bone tissue (referred to herein as CT bone images) of head 41.

In some embodiments, in CT image acquisition step 100, processor 34 may receive a volumetric image (e.g., having voxels) of at least part of head 41 having the predefined locations. In such embodiments, processor 34 is configured to select, from the volumetric image, at least a slice comprising one or more of the predefined locations. In an embodiment, the selected slice may have all the predefined locations. In another embodiment, processor 34 may select multiple slices comprising together all the predefined locations.

At a registration tool attachment step 102, physician 24 positions wand 30 sequentially at gap 99 from one or more of the multiple predefined locations on patient head 41. Note that the subsequent steps (104-110) described below, is carried out at each of these predefined locations.

At a position calculation step 104, processor 34 receives the position measurement from position sensor 77 and calculates the position of transducer 66 in the coordinate system of the position tracking system. At an US measurements step 106, system 20 activates transducer 66 so as to acquire US measurements. At a tissue position calculation step 108, processor 34 receives the position signals from transducer 66 and the TOF measurement from transducer 66, and calculates the US coordinate, e.g., the position of the skin tissue in the coordinate system of the position tracking system. At a CT tissue identification step 110, processor 34 identifies the corresponding CT coordinate, e.g., the position of the skin tissue in CT image 35, using any suitable technique known in the art. As noted above, steps 104-110 are repeated for each of the predefined locations.

At a registration step 112, processor 34 registers CT image 35 with the coordinate system of the position tracking system by correlating between the US skin coordinates and the corresponding CT skin coordinates at the predefined locations in head 41.

As described in FIG. 2 above, processor 34 is configured to carry out the registration method described above (mutatis mutandis) using US bone coordinates and CT bone coordinates of one or more of the predefined locations. Note that processor 34 may use the bone coordinates instead of, or in addition to, the skin coordinates, so as to improve the registration accuracy between the coordinate systems of image 35 and the position tracking system.

Although the embodiments described herein mainly address sinuplasty procedures, the methods and systems described herein can also be used in other applications and/or in other organs. For example, in orthopedic procedures, in which physician 24 may position wand 30 sequentially at multiple predefined locations on an external surface (e.g., skin tissue) of an orthopedic organ (e.g., hand) of patient 22, while maintaining a gap from skin tissue. Note that the methods and system described above may also be used, mutatis mutandis, in organs having soft tissue without bone tissue.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:

receiving multiple measurements, which are acquired using a registration tool comprising an ultrasound (US) transducer and a position sensor of a position-tracking system, wherein the measurements are acquired by positioning the registration tool, while maintaining a gap from skin tissue, at multiple respective locations on a patient head and acquiring respective position measurements of the position sensor and respective US measurements of the skin tissue at the locations;

calculating first positions of the skin tissue at the multiple locations, based on the position measurement and the US measurements obtained using the registration tool;

identifying second positions of the skin tissue at the multiple locations, in an anatomical image of the patient head; and registering the anatomical image with a coordinate system of the position tracking system, by correlating the first positions and the second positions, so as to enable tracking a medical instrument, which is inserted into the patient head and comprises another position sensor of the position-tracking system, using the anatomical image registered with the position-tracking system.

2. The method according to claim 1, and comprising acquiring respective position measurements of the position sensor and respective US measurements of bone tissue at the locations, wherein calculating the first positions comprises calculating first bone positions of the bone tissue at the multiple locations, and wherein identifying the second positions comprises identifying second bone positions of the bone tissue at the multiple locations.

3. The method according to claim 1, wherein the US transducer is disposed at a fixed displacement relative to the position sensor, and wherein calculating the first positions comprises considering the fixed displacement in calculation of the first positions.

4. The method according to claim 1, wherein the anatomical image comprises one or more computerized tomography (CT) images.

5. The method according to claim 1, wherein the locations comprise locations of skin tissue covering bone features selected from a list consisting of a cheek bone protrusion, a bridge of a nose, a tip of the nose and a chin.

6. The method according to claim 1, wherein receiving the US measurements comprises receiving round-trip propagation times of US pulses traversing, at one or more of the locations, between a tip of the registration tool and the skin tissue of the patient head.

7. The method according to claim 1, wherein the locations comprise locations of skin tissue covering bone features, wherein receiving the US measurements comprises receiving given round-trip propagation times of US pulses traversing, at one or more of the locations, between a tip of the registration tool and the bone features of the locations, and comprising, using the given round-trip propagation times for registering the anatomical image with the coordinate system of the position tracking system.

8. The method according to claim 1, wherein the medical instrument comprises a sinuplasty catheter.

9. The method according to claim 1, wherein the registration tool comprises a handheld wand.

10. The method according to claim 1, wherein the multiple measurements are acquired at a given temperature and a given humidity, and comprising calibrating the registration tool to compensate for a change in the US measurements caused by a deviation from at least one of the given temperature and the given humidity.

11. An apparatus, comprising:

a registration tool, comprising:

an ultrasound (US) transducer, which is configured, when the registration tool is positioned sequentially, while maintaining a gap from skin tissue, at multiple respective locations on a patient head, to acquire respective US measurements of the skin tissue at the locations; and a position sensor of a position-tracking system, which is configured to acquire respective position measurements of the registration tool at the locations; and a processor, which is configured to:

receive the multiple US measurements and the respective position measurements acquired by the registration tool;

calculate first positions of the skin tissue at the multiple locations, based on the position measurements and the US measurements;

identify second positions of the skin tissue at the multiple locations, in an anatomical image of the patient head; and register the anatomical image with a coordinate system of the position tracking system, by correlating the first positions and the second positions, so as to enable tracking a medical instrument, which is inserted into the patient head and comprises another position sensor of the position-tracking system, using the anatomical image registered with the position-tracking system.

12. The apparatus according to claim 11, wherein the registration tool is configured to acquire respective position measurements of the position sensor and respective US measurements of bone tissue at the locations, wherein the processor is configured to calculate first bone positions of the bone tissue at the multiple locations, and to identify second bone positions of the bone tissue at the multiple locations.

13. The apparatus according to claim 11, wherein the US transducer is disposed at a fixed displacement relative to the position sensor, and wherein the processor is configured to consider the fixed displacement in calculation of the first positions.

14. The apparatus according to claim 11, wherein the anatomical image comprises one or more computerized tomography (CT) images.

15. The apparatus according to claim 11, wherein the locations comprise locations of skin tissue covering bone features selected from a list consisting of a cheek bone protrusion, a bridge of a nose, a tip of the nose and a chin.

16. The apparatus according to claim 11, wherein the multiple US measurements comprise round-trip propagation times of US pulses traversing, at one or more of the locations, between a tip of the registration tool and the skin tissue of the patient head.

17. The apparatus according to claim 11, wherein the locations comprise locations of skin tissue covering bone features, and wherein the processor is configured to: (a) receive given round-trip propagation times of US pulses traversing, at one or more of the locations, between a tip of the registration tool and the bone features of the locations, and (b) use the given round-trip propagation times, for registering the anatomical image with the coordinate system of the position tracking system.

18. The apparatus according to claim 11, wherein the medical instrument comprises a sinuplasty catheter.

19. The apparatus according to claim 11, wherein the registration tool comprises a handheld wand.

20. The apparatus according to claim 11, wherein the US transducer is configured to acquire the multiple measurements at a given temperature and a given humidity, and comprising a jig for calibrating the registration tool to compensate for a change in the US measurements caused by a deviation from at least one of the given temperature and the given humidity.

* * * * *